(12) United States Patent
Alexander et al.

(10) Patent No.: US 7,758,384 B2
(45) Date of Patent: Jul. 20, 2010

(54) IMPLANTABLE BIFURCATED NEUROSTIMULATOR ADAPTERS

(75) Inventors: James A. Alexander, Shorewood, MN (US); Mark J. Holle, Shoreview, MN (US); Robyn L. Jagler, Eagan, MN (US); Jason D. Rahn, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 713 days.

(21) Appl. No.: 11/678,716

(22) Filed: Feb. 26, 2007

(65) Prior Publication Data

US 2008/0208267 A1 Aug. 28, 2008

(51) Int. Cl.
*A61N 1/375* (2006.01)
(52) U.S. Cl. .................... 439/623; 607/37; 439/909
(58) Field of Classification Search ........... 439/668, 439/669, 502, 623, 909; 607/36, 37, 38
See application file for complete search history.

(56) References Cited

U.S. PATENT DOCUMENTS

| | | | |
|---|---|---|---|
| 5,328,442 A | | 7/1994 | Levine |
| 5,546,950 A | * | 8/1996 | Schoeckert et al. ......... 600/508 |
| 5,797,970 A | | 8/1998 | Pouvreau |
| 6,895,276 B2 | * | 5/2005 | Kast et al. .................. 607/37 |
| D525,708 S | | 7/2006 | Jones et al. |
| 7,128,600 B2 | | 10/2006 | Osypka |
| 7,242,987 B2 | * | 7/2007 | Holleman et al. .......... 607/122 |
| 7,563,141 B2 | * | 7/2009 | Alexander et al. .......... 439/669 |
| 7,594,828 B2 | * | 9/2009 | Alexander et al. .......... 439/669 |
| 2004/0034392 A1 | | 2/2004 | Spadgenske |
| 2004/0260355 A1 | | 12/2004 | Holleman et al. |
| 2004/0260373 A1 | | 12/2004 | Ries et al. |

OTHER PUBLICATIONS

Medtronic, Neurostimulation Systems, Expanding the Array of Pain Control Solutions, Brochure 1999, (UC199901189EN NI-3764EN).
PCT Application No. PCT/US2008/053900 International Search Report and Written Opinion, dated Jun. 13, 2008, 8 pages.

* cited by examiner

*Primary Examiner*—Neil Abrams
(74) *Attorney, Agent, or Firm*—Fredrikson & Byron, P.A.

(57) ABSTRACT

An adapter for coupling a pair of implantable neurostimulator lead extension plugs to a connector port of a neurostimulator device includes a connector coupled to a first end of an elongate body and a flexible bifurcation member coupled to a second end of the elongate body, wherein the bifurcation member includes a first branch, to which a first housing, having first and second ports, is coupled, and a second branch, to which a second housing, having first and second ports, is coupled. Openings of the first and second ports of each housing provide for side-by-side insertion of first and second connector terminals of one of the lead extension plugs. Contacts within each port provide for electrical coupling with corresponding contacts of the connector terminals of the plug, and are coupled to corresponding contacts of the adapter connector via conductors extending within the elongate body between the corresponding housing and connector.

55 Claims, 6 Drawing Sheets

IMPLANTABLE BIFURCATED NEUROSTIMULATOR ADAPTERS

RELATED APPLICATION

The present patent application is related to the commonly assigned patent application entitled IMPLANTABLE NEUROSTIMULATOR ADAPTERS, Ser. No. 11/678,706, now U.S. Pat. No. 7,594,828, is filed concurrently herewith, and is hereby incorporated, by reference, in its entirety.

TECHNICAL FIELD

The present invention pertains to extending implantable neurostimulator leads and more particularly to adapters for neurostimulator lead extensions.

BACKGROUND

Implantable neurostimulators can provide electrical stimulation for the treatment of pain and/or various neurological disorders. Neurostimulators typically include one or more stimulation electrodes which may be implanted at specific sites along a spinal cord, a peripheral nerve, or in a brain of a patient; the one or more electrodes are typically mounted to an elongate lead body which carries corresponding conductors for electrical coupling of the electrodes to a neurostimulator device. Because the neurostimulator device is usually implanted in a subcutaneous pocket that is somewhat remote from the stimulation site, often times a lead extension is required to couple a lead connector, which terminates a proximal end of the lead body, to the device. The extension provides an additional length of conductor(s) to reach the device for the electrical coupling of the one or more lead electrodes. One or more connector terminals terminating a proximal end of the lead extension are configured to mate with corresponding connector ports of the device.

In recent years, new models of neurostimulator devices have been developed for increased functionality; modifications to the size and/or shape of these newer devices have been made, for example, to accommodate additional components, while keeping a bulk of the devices to a minimum. In many instances, the modifications have been accompanied by changes to the configuration of the connector ports of these devices so that the ports are no longer compatible with connector terminals of lead extensions which were designed to couple with older style devices. Thus, for those patients who either require or desire that an older style device be exchanged for a newer device, there is a need for an adapter to couple the connector terminals of one or more previously implanted lead extensions to one or more ports of the newer device.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
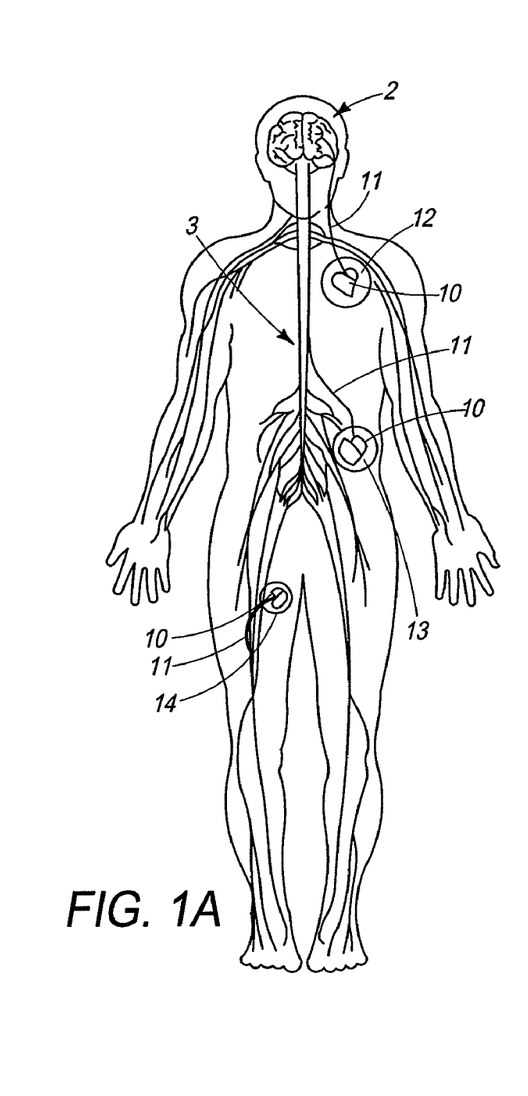
FIG. 1A is schematic plan view of a human body showing various general implant locations for implantable neurostimulator systems.

FIG. 1A is schematic plan view of a human body showing various general implant locations for implantable neurostimulator systems. FIG. 1A illustrates three general types of neurostimulator systems including devices 10 each coupled to an elongate lead 11. A first of devices 10 is shown implanted in a pectoral region 12, for example, within a subcutaneous pocket, and corresponding lead 11 extending from device 10 to a site within a brain 2; a second of devices 10 is shown implanted in a lower region 13 of the body, and corresponding lead 11 extending from device 10 to a site along a spinal cord 3; a subcutaneous pocket in lower region 13 may be formed, in an anterior, abdominal area of the body, or in a posterior, high buttocks area of the body. A third of devices 10 is shown implanted in a subcutaneous pocket form in a thigh region 14 of the body, and a corresponding lead 11 is shown extending from device 10 to a peripheral nerve site in a leg of the body. It should be noted that any of the pockets in regions 12, 13, 14 may hold a device coupled to a lead extending to any of the peripheral nerves, for example, in either leg, in either arm, or in the neck or head. Although not shown, those skilled in the art will understand that leads 11 each include one or more electrodes in proximity to a distal end thereof.

Figure 1B:
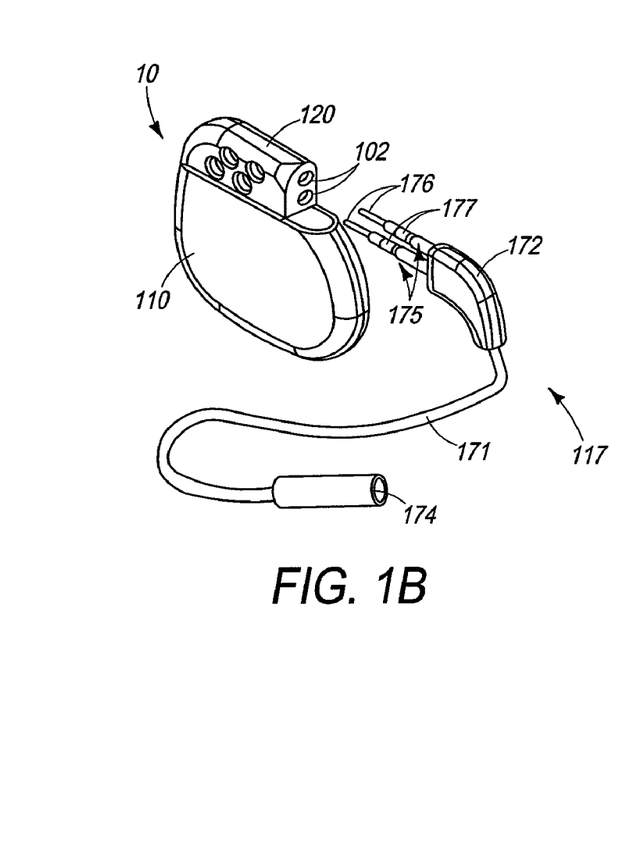
FIG. 1B is a perspective view of a portion of an exemplary implantable neurostimulator.

As previously described, a length of each of leads 11 may be extended by a lead extension. FIG. 1B is a perspective view of device 10 and an exemplary lead extension 117. FIG. 1B illustrates device 10 including a housing or can 110 and a connector module 120 coupled to can 110 and including two connector ports 102; can 110 houses a battery and electronic circuitry necessary to provide electrical stimulation delivered by the electrodes of leads 11. Those skilled in the art understand that electrical contacts within each of ports 102 are electrically coupled, via hermetically sealed feedthroughs, to the electrical circuitry housed within can 110. FIG. 1B further illustrates lead extension 117 including an elongate body 171, to which a plug 172 is coupled at a proximal end, and to which a connector port 174 is coupled at a distal end. A pair of connector terminals 175 is shown extending proximally from plug 172; each of connector terminals 175 includes a terminal pin contact 176 and a contact surface 177, which is spaced apart from pin contact 176 along a length of the corresponding connector terminal 175.

According to the illustrated embodiment, ports 102 of device connector module 120 are positioned to receive, for electrical and mechanical coupling, the pair of side-by-side connector terminals 175, and, extension connector port 174 is adapted to receive, for electrical and mechanical coupling, a lead connector, for example, an in-line connector, such as is known to those skilled in the art, which terminates a proximal end of the lead and includes a plurality of spaced apart contacts. Those skilled in the art will appreciate that extension port 174 includes a plurality of electrical contacts, which couple with the contacts of the lead connector, when the connector is fully inserted in port 174, and which are each coupled either to a corresponding terminal pin contact 176 or to a corresponding contact surface 177 of connector terminals 175, via a corresponding elongate conductor extending within elongate body 171. Thus, when connector terminals 175 are fully inserted into device ports 102, and the lead connector is fully inserted into extension portion 174, electrical stimulation therapy may be delivered from device 10 to the one or more electrodes of lead 11, either implanted in brain 2, or along spinal cord 3, or along a peripheral nerve (FIG. 1A).

Figure 2A:
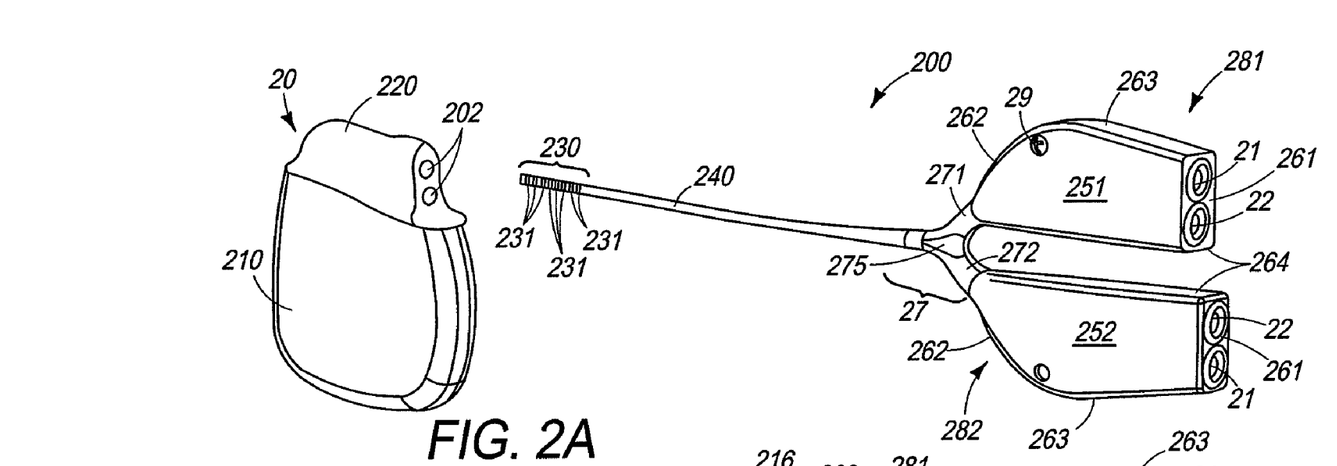
FIG. 2A is a perspective view of a neurostimulator adapter and a corresponding neurostimulator device, according to some embodiments of the present invention.

FIG. 2A is a perspective view of a neurostimulator adapter 200 and a corresponding neurostimulator device 20, according to some embodiments of the present invention. FIG. 2A illustrates device 20, like device 10 (FIG. 1B), including a housing or can 210 and a connector module 220, however connector module 220 includes ports 202 which differ in individual size and configuration from ports 102 of device 10. According to embodiments of the present invention, when device 10 (FIG. 1B) is changed out for device 20, an adapter, for example, adapter 200, is necessary to provide a compatible coupling between one of ports 202 of device 20 and the previously implanted extension 117.

With reference to FIG. 2A, adapter 200 includes an elongate body 240 to which a connector 230, which is compatible with each of ports 202 of device 20, is coupled; connector 230 is shown including eight contacts 231, so it should be appreciated that each of ports 202 include a corresponding set of eight device contacts for electrical coupling with contacts 231, when connector 230 is fully inserted therein. FIG. 2A illustrates adapter 200 including a flexible bifurcation member 27 coupled to a distal end of body 240; bifurcation member 27 includes a first branch 271, to which a first housing 281 is coupled, a second branch 272, to which a second housing 282 is coupled, and a bending joint 275 located between first and second branches 271, 272. FIG. 2A further illustrates each housing 281, 282 including a first sidewall 251, a second sidewall 252, opposite first sidewall 251, a first face 261 extending between first and second sidewalls 251, 252, a second face 262, opposite first face 261 and extending between first and second sidewalls 251, 252, a third face 263 extending between first and second sidewalls 251, 252 and between first and second faces 261, 262, a fourth face 264, opposite third face 263 and extending between first and second sidewalls 251, 252 and between first and second faces 261, 262, a first port 21 and a second port 22.

Figure 2B:
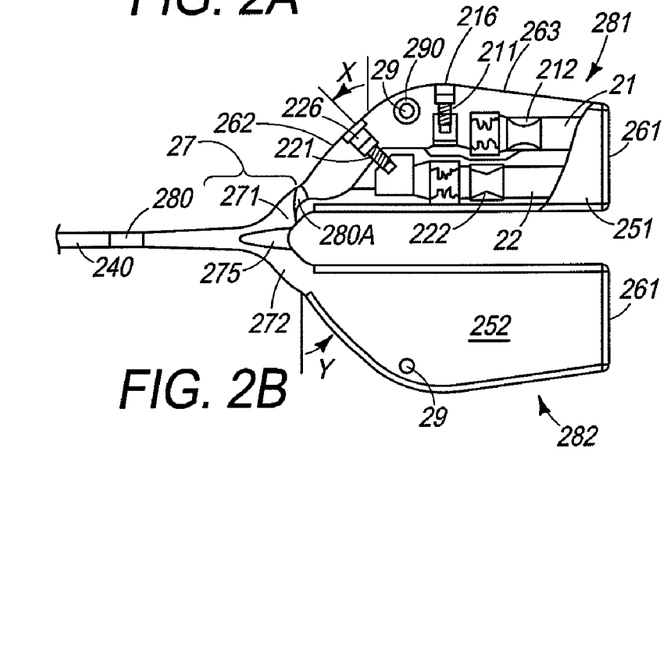
FIG. 2B is a plan view including a partial cut-away sections of the adapter shown in FIG. 2A, according to some embodiments.

FIG. 2B is a plan view including partial cut-away sections of adapter 200, according to some embodiments. FIG. 2B illustrates ports 21, 22 of housing 281 each including a spring-type housing contact 212, 222, for example, a multi-beam contact, which may be formed from stainless steel, MP35N alloy, titanium or any other suitable material known to those skilled in the art, and a set screw-type housing contact, which may likewise be formed from stainless steel, MP35N alloy, titanium or any other suitable material known to those skilled in the art, and which includes a set screw 211, 221 mounted in a set screw block. FIG. 2B further illustrates a shaft of first port set screw 211 extending approximately parallel with first face 261, while a shaft of second port set screw 221 extends at an angle X, for example, greater than 0 degrees and less than 90 degrees, with respect to first face 261. An access port 216 for set screw 211 is shown located on third face 263, and an access port 226 for set screw 221 is shown located on second face 262. Those skilled in the art will understand that access ports 216, 226 provide access for a set screw wrench, to engage screws 211, 221, respectively, yet are sealed to prevent ingress of bodily fluids when adaptor 200 is implanted; any suitable type of grommet known to those skilled in the art and through which a set screw wrench may pierce, may be employed by embodiments of the present invention. With reference to FIG. 2B, in conjunction with FIG. 1B, it should be appreciated that when each connector terminal 175 of extension plug 172 is fully inserted into a corresponding port 21, 22, each contact surface 177 mates with a corresponding spring contact 212, 222 and each terminal pin contact 176 is positioned to mate with a corresponding set screw 211, 221. Although not labeled in FIG. 2B, those skilled in the art will recognize a set of sealing rings shown in each of ports 21, 22. The illustrated sealing rings are intended to provide electrical isolation between each pin contact 176 and corresponding contact surface 177 of fully inserted terminals 175, but are not necessary elements for every embodiment of the present invention. It should be noted that, according to preferred embodiments, ports 21, 22 of housing 282 include the housing contacts described above and are configured like ports 21, 22 of housing 281. Furthermore, it should be noted that the scope of the present invention is not limited to the illustrated types of contacts and alternate embodiments of the present invention may include any other types of contacts known to those skilled in the art.

According to the illustrated embodiment: first and second ports 21, 22 of each housing 281, 282 have openings located on first face 261 thereof, in order to receive insertion of side-by-side connector terminals 175 of extension 117 (FIG. 1B); first and second sidewalls 251, 252 each include a relatively flat outer surface extending alongside each of ports 21, 22; and second face 262 extends at an angle Y, for example, greater than 0 degrees and less than 90 degrees, with respect to first face 261. It may be appreciated that the angled arrangement of set screws 221, in combination with the angling of second faces 262, contributes to a reduction in a bulk of each of housings 281, 282 from a bulk that would have resulted if set screws 221 had been oriented in a traditional manner, for example, like set screws 211, such that their shafts extended parallel to first faces 261. Such a traditional arrangement of set screws 221 would have forced an increased footprint of each of housings 281, 282, for example, along second faces 242 (to provide appropriately oriented access ports for the set screw along second faces 262), or would have forced an increased thickness of each of housings 281, 282, between sidewalls 251, 252 (to provide appropriately oriented access ports along one or both of sidewalls 251, 252).

FIG. 2B illustrates a group of eight conductors 280, for example, individually insulated cable conductors, that extend within body 240 from connector 230 to bifurcation member 27. A first subgroup 280A of four conductors from group 280 is shown extending through first leg 271 of bifurcation member 27 and into first housing 281 in order to couple each of a first four of contacts 231 of connector 230 to the corresponding housing contact within one of ports 21, 22 of housing 281, and, although not shown, it will be appreciated that a second group of four conductors from group 280 extends through second leg 272 of member 27 and into second housing 282 in order to couple a second four of connector contacts 231 to the corresponding housing contacts within one of ports 21, 22 of housing 282. Conductors 280 may extend within body 240 in either a straight or coiled configuration, and body 240 may include either a single or multi-lumen tube, for example, formed, by an extrusion and/or molding process, from medical grade silicone, or polyurethane, or a combination thereof. Likewise, bifurcation member 27 may be formed, by an extrusion and/or molding process, from silicone, polyurethane, or a combination thereof. Conductors 280 are preferably formed from an MP35N alloy, which is known to those skilled in the art; and each of conductors 280 is coupled to a corresponding connector contact 231 by means known to those skilled in the art, for example, crimping and/or welding; and each of conductors 280 is preferably individually insulated by an insulative jacket, for example, formed from a fluoropolymer or a polyimide. FIG. 2B further illustrates conductor paths (not labeled) extending within housing 281 from each of spring-type housing contacts 211, 212 and the set screw-type housing contacts toward first leg 271 of bifurcation member 27, and, it should be understood that, similar paths extend within housing 282, according to preferred embodiments. Those skilled in the art will appreciate that conductors 280 may be electrically coupled to the housing contacts in a number of ways; for example, each conductor of each of the first and second subgroups may be routed into the respective housing 281, 282 along a corresponding conductor path for direct coupling with the corresponding contact, for example, via welding, or, a separate conductor may extend from each contact, along the corresponding conductor path to a corresponding coupling plate located in proximity to second face 262 for coupling to the corresponding conductor of group 280, for example, via welding. Those skilled in the art will further appreciate that appropriate electrical isolation may be provided for each conductor within housings 281, 282, either via an insulative jacket formed about each conductor, or via insulative walls formed within housings 281, 282 between each conductor, or via a combination thereof.

FIGS. 2A-B further illustrate each of housings 281, 282 including an optional hole 29, which extends through each housing 281, 282 from first sidewall 251 to second sidewall 252, and which is located in proximity to an intersection of second housing face 262 and third housing face 263. Hole 29 may be used to facilitate securing, for example, via a suture, of adapter housings 281, 282 to tissue within an implant pocket, either alongside device 20 or separate from device 20.

According to an exemplary embodiment of the present invention, each of housings 281, 282 is formed from medical grade silicone, preferably having a durometer of approximately 65D. With reference to FIG. 2B, a reinforcing tubing or liner 290 that extends within hole 29 may be desirable, particularly when housing 24 is formed from a relatively soft material that requires a harder interface, for example, for a suture to bear against; examples of appropriate materials for liner 290 include, without limitation, polysulfone and a relatively hard durometer of polyurethane, for example, 75D. Each of housings 281, 282 may be molded and the illustrated components assembled therein according to any suitable method known to those skilled in the art. According to an exemplary assembly method, a portion of each of housings 281, 282 is molded with openings into which the components are inserted; conductors may be coupled to each of the housing contact components either before or after insertion into the corresponding opening of the corresponding housing. After the conductors are routed along the conductor paths, voids over and around each opening are filled in, either by a secondary molding process or manual injection of filler material, for example, medical grade silicone.

Figure 2C:
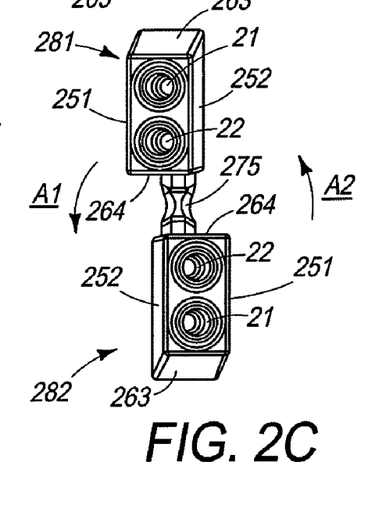
FIG. 2C is an end view of the adapter shown in FIG. 2A, according to some embodiments.
Figure 2D:
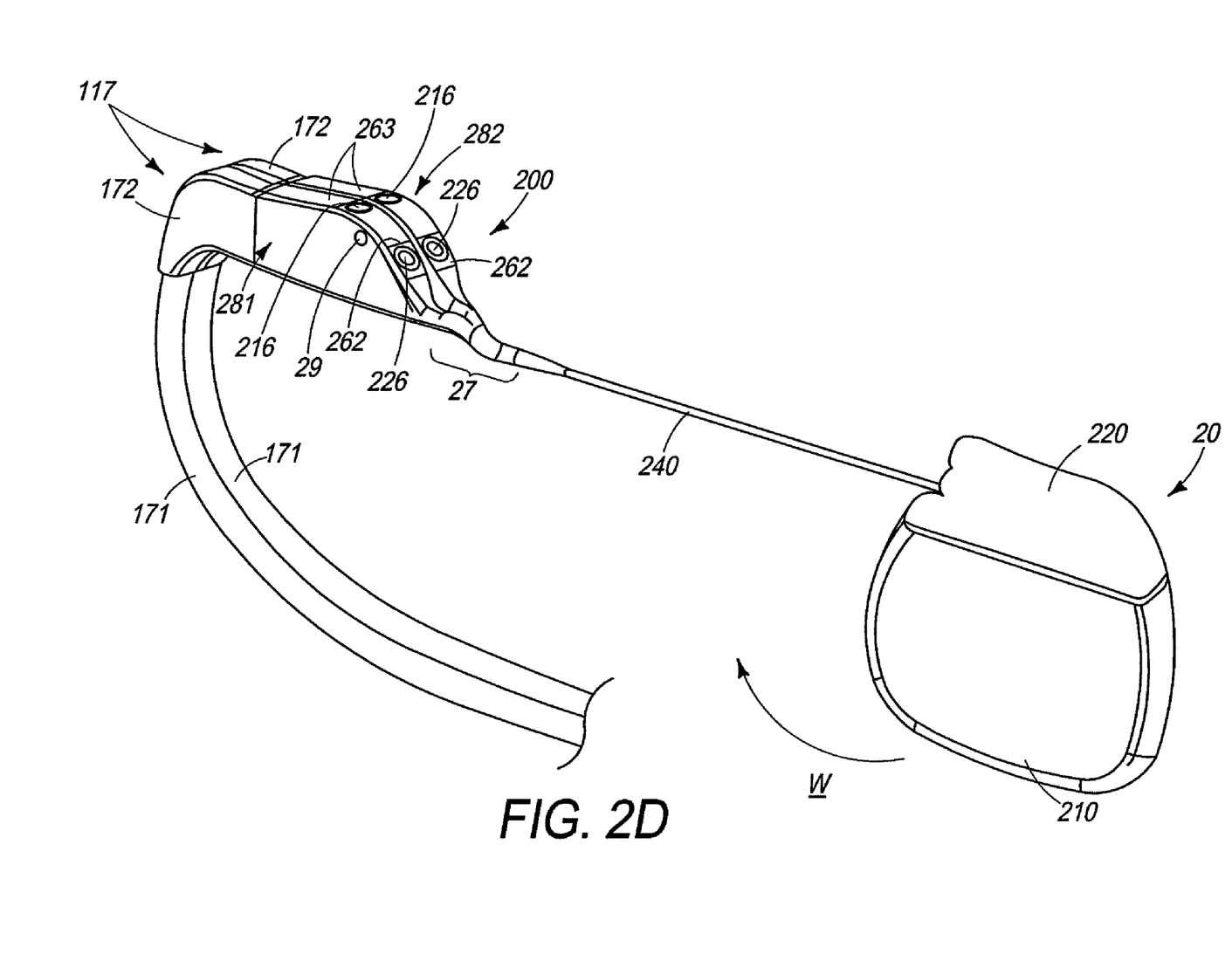
FIG. 2D is a perspective view of a portion of a system including the adapter and device of FIG. 2A, according to some embodiments of the present invention.

FIG. 2C is an end view of adapter 200, according to some embodiments; and FIGS. 2A-C illustrate flexible bifurcation member 27 of adaptor 200 in a relaxed state, or un-deformed, such that fourth face 264 of housing 281 faces in a generally opposite direction to that in which fourth face 264 of housing 282 faces. A deformation of bifurcation member 27, for example, by folding one of first and second housings 281, 282 over, per arrow A1 or A2 (FIG. 2C), will allow for an alternate alignment of housings 281, 282, for example as is illustrated in FIG. 2D. According to the illustrated embodiment, bending joint 275 of bifurcation member 27 allows first and second housings 281, 282 to be moved from the configuration shown in FIGS. 2A-C to the configuration shown in FIG. 2D, such that first sidewall 251 of housing 281 is adjacent to, and faces, second sidewall 252 of second housing 282, and first ports 21 of first and second housings 281, 282 are beside one another and second ports 22 of first and second housings 281, 282 are beside one another. Bending joint 275 may be formed in bifurcation member 27, for example, by a soft section or by a thinned section, like a crease, which is shown in the embodiment of FIGS. 2A-C. With reference to FIG. 2D, it will be appreciated that hole 29 of first housing 281 is aligned with hole 29 of second housing 282, when flexible bifurcation joint 275 is deformed to bring first sidewall 251 of housing 281 alongside second sidewall 252 of housing 282; thus, a securing member passed through holes 29 of first and second housings 281, 282 can, in addition to securing each housing 281, 282 to subcutaneous tissue, secure housings 281, 282 in close proximity with one another.

FIG. 2D further illustrates two extensions 117 (FIG. 1B) plugged into adapter 200, which couples extensions 117 to device 20, via insertion of adapter connector 230 into one of device ports 202 (FIG. 2A). Although adapter 200 is illustrated in FIG. 2D with housings 281, 282 folded together, it should be appreciated that adapter 200 may couple extensions 117 to device 20 and be implanted without housings 181, 182 being folded together. Furthermore, it should be noted that, although device 20 has been illustrated having two connector ports 202, device need only have one of these ports 202.

According to some exemplary implant methods, extensions 117 are plugged into adapter 200, either before or after adapter 200 is plugged into device 20, and either before or after housings 281, 282 have been folded toward one another, then device 20 may be rotated around, per arrow W, and shifted alongside adapter 200 and extension plugs 172 such that elongate body 240 of adapter 200 wraps approximately around a perimeter of device 20. A length of elongate body 240 and bifurcation member 27, together, may be between approximately 10 centimeters and approximately 20 centimeters to accommodate such an implanted configuration. An implanter may desire to secure, for example, with a suture through holes 29, adapter housings 281, 282 to subcutaneous tissue within an implant pocket alongside device 20 such that housings 281, 282 will remain either beside or behind device 20 in the pocket, rather than between device 20 and the skin of the body. Such an arrangement is preferred if a battery of device 20 has the capacity to be re-charged transcutaneously, and for added protection of adapter 200 and extensions 117 from nicks and cuts, if, and when and explant of device 20 is required, at a later date.

According to alternate implant methods, adapter 200 may be implanted in a first subcutaneous pocket and device 20 in a second subcutaneous pocket; for example, the first pocket may be one previously formed for a device which has been explanted to be exchanged for device 20, and the second pocket, a new pocket formed for device 20. With reference back to FIG. 1A, the first pocket may be in pectoral region 12 and the second pocket in lower region 13 or thigh region 14. For such an implant configuration in which there is a relatively significant distance between the two pockets, a length of body 240 and bifurcation member 27, together, is preferably greater than approximately 40 centimeters, upwards to approximately 110 centimeters.

Figure 3A:
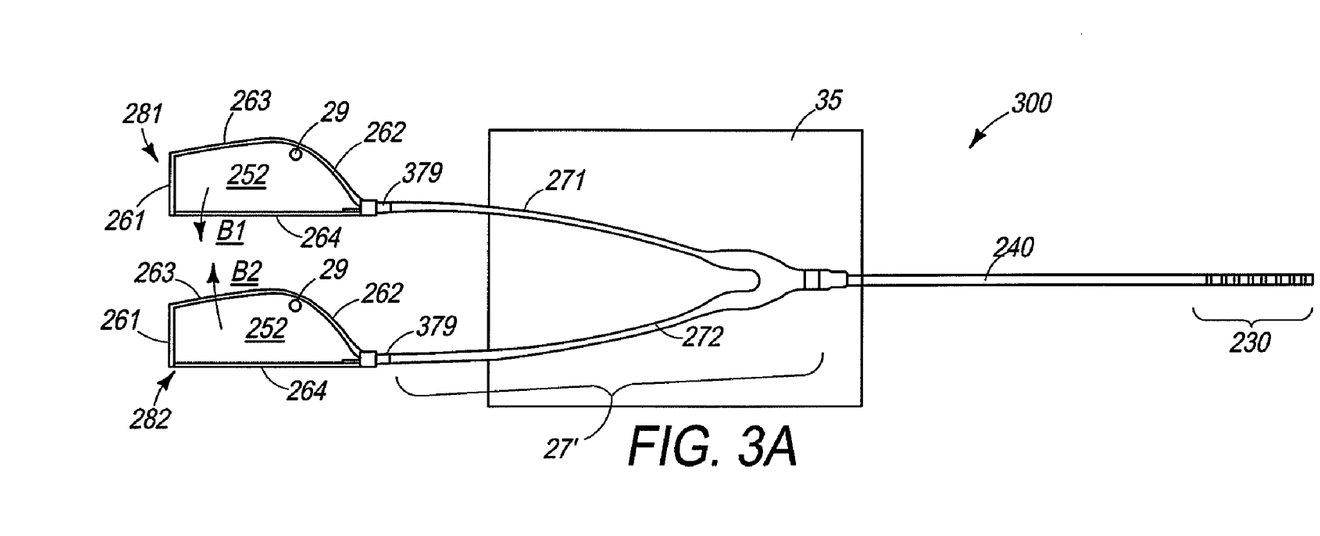
FIG. 3A is a plan view of a neurostimulator adapter, according to some alternate embodiments of the present invention.
Figure 3B:
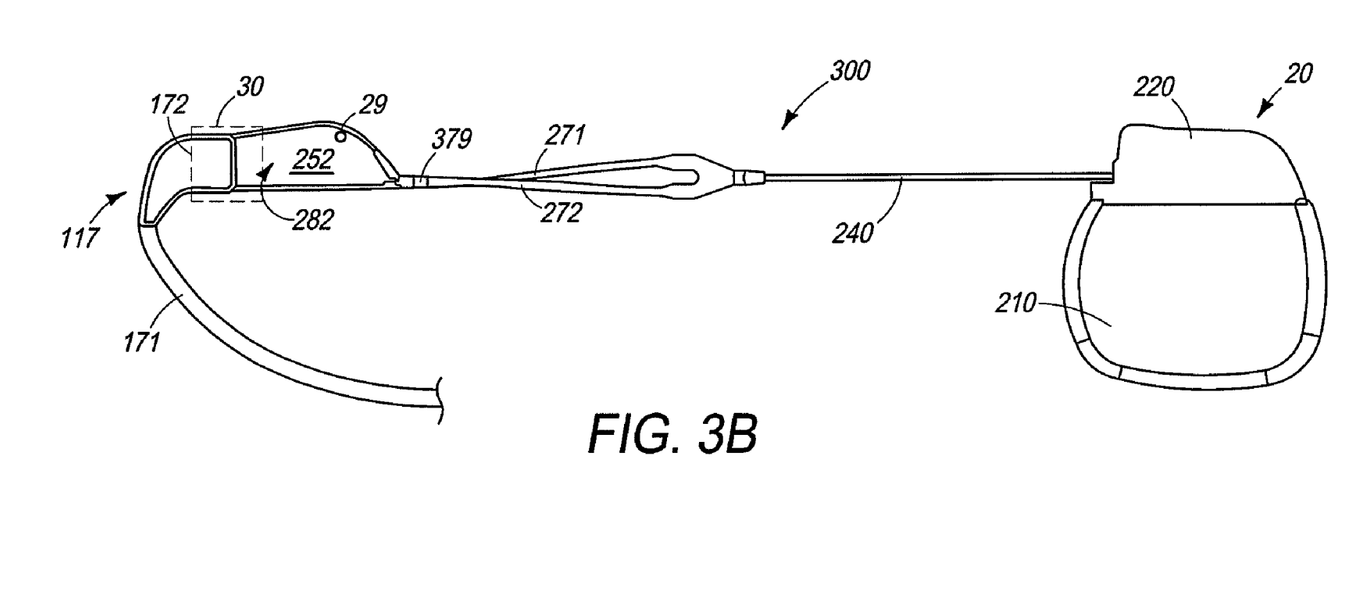
FIG. 3B is a plan view of a portion of a system including the adapter of FIG. 3A, according to some embodiments of the present invention.

FIG. 3A is a plan view of a neurostimulator adapter 300, according to some alternate embodiments of the present invention. FIG. 3A illustrates adapter 300 including, like adapter 200, connector 230 coupled to a proximal end of elongate body 240, and each of first and second housings 281, 282 coupled to a corresponding branch 271, 272 of a flexible bifurcation member 27', which is coupled to a distal end of elongate body 240. In contrast to adapter 200, bifurcation member 27' of adapter 300 need not include a bending joint, like joint 275 (FIGS. 2A-C), since branches 271, 272 of adapter 300 are of a length and flexibility to allow for movement of housings 281, 282, for example, per one or both of arrows B1, B2, into a side-by-side configuration as illustrated in FIG. 3B. FIG. 3B is a plan view of a portion of a system including adapter 300, according to some embodiments, and illustrates adapter 300 coupling at least one extension 117 to device 20 in a similar manner to that described for adapter 200 in conjunction with FIG. 2D. In further contrast to adapter 200, housings 281, 282 of adapter 300 are shown oriented such that fourth face 264 of each faces in a same general direction, when bifurcation member 27' is not deformed (FIG. 3A), for example, by bending and/or twisting of one or both branches 271, 272, as well as when branches 271, 272 are bent to allow housings 281, 282 to come together (FIG. 3B). With reference to FIG. 3B, it should be appreciated that hole 29 of each housing 281, 282 may be aligned in order to secure housings 281, 282, together, to subcutaneous tissue, for example, in a manner previously described for adapter 200. FIGS. 3A-B further illustrate each leg 271, 272 including an optional groove 379 formed therein in proximity to the corresponding housing 281, 282; groove 379 may further facilitate securing of housings 281, 282 by providing a reinforced zone in each branch 271, 272 about which a suture may be tied. Exemplary implant methods for the system shown in FIG. 3B are similar to those previously described for the system described in conjunction with FIG. 2D.

FIG. 3A further illustrates a plane 35, in which branches 271, 272 of bifurcation member 27' extend; according to the illustrated embodiment, first and second sidewalls 251, 252 of each housing 281, 282 extend approximately parallel to plane 35 when bifurcation member 27' is un-deformed. According to an alternate embodiment, for example, adapter 300' shown in FIG. 3C, housings 281, 282 are oriented such that sidewalls 251, 252 extend approximately parallel to a plane 37, which extends at an angle Z with respect to plane 35, when bifurcation member 27' is un-deformed. Angle Z is preferably approximately 90 degrees, but may be any angle greater than 0 degrees.

Figure 3C:
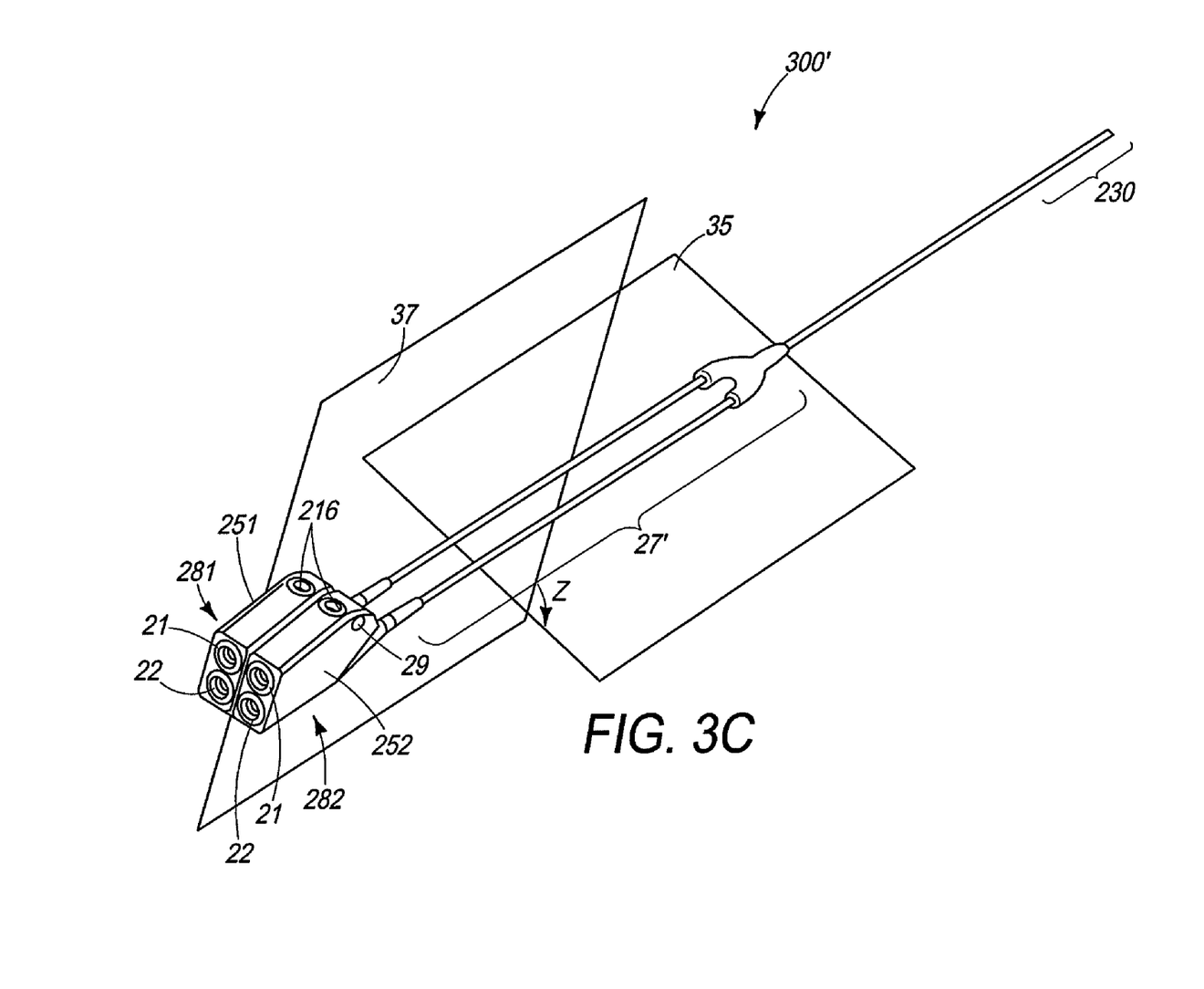
FIG. 3C is a perspective view of an adapter, according to some other embodiments of the present invention.
Figure 4A:
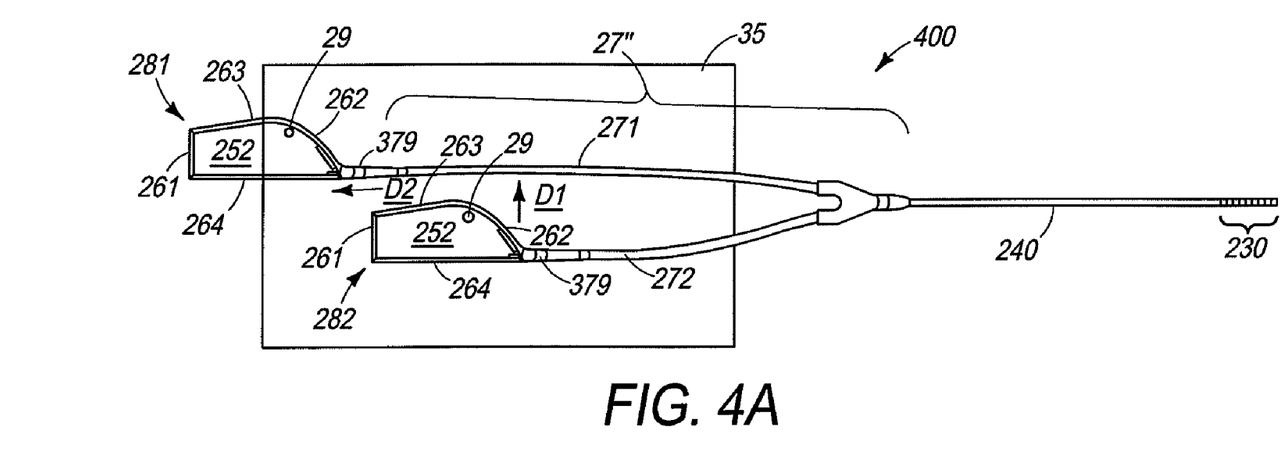
FIG. 4A is a plan view of a neurostimulator adapter, according to yet further embodiments of the present invention.
Figure 4B:
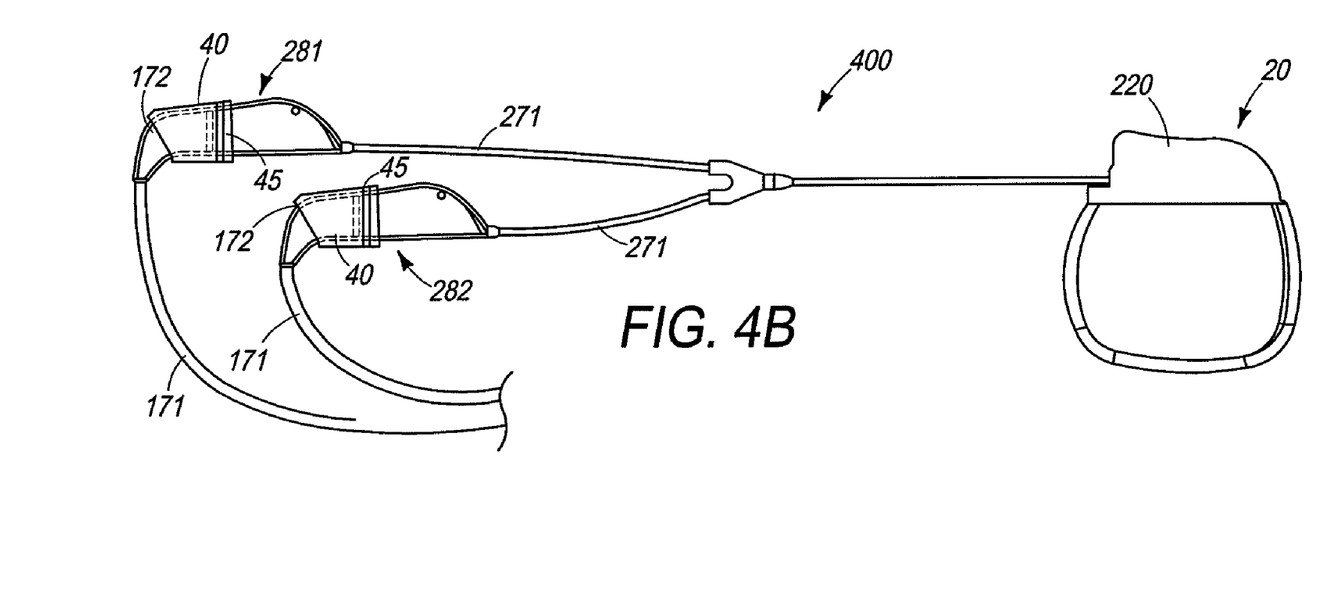
FIG. 4B is a plan view of a portion of a system including the adapter of FIG. 4A, according to some embodiments of the present invention.

FIG. 4A is a plan view of a neurostimulator adapter 400, according to yet further embodiments of the present invention. FIG. 4A illustrates adapter 400 including, like adapter 300, connector 230 coupled to a proximal end of elongate body 240, and each of first and second housings 281, 282 coupled to a corresponding branch 271, 272 of a flexible bifurcation member 27", which is coupled to a distal end of elongate body 240. Like bifurcation member 27' of adapter 300, member 27" of adapter 400 does not include a bending joint, like joint 275 (FIGS. 2A-C), but, unlike member 27' of adapter 300, a length of branch 271 is greater than that of branch 272 such that housing 281 is offset from housing 282, in both directions D1 and D2 along plane 35, when bifurcation member 27" is un-deformed. It should be noted that, according to alternate embodiments, a length of branch 271 is less than a length of branch 272 so that housing 281 is offset from housing 282 in a direction opposite to D1. FIG. 4B is a plan view of a portion of a system including adapter 400, according to some embodiments, and illustrates adapter 400 coupling extensions 117 to device 20. Exemplary implant methods for the system shown in FIG. 4B are similar to those for the system described in conjunction with FIG. 2D. However, in contrast to adapters 200, 300 and 300', where, according to preferred embodiments, housings 281, 282 are allowed to come together, such that second sidewall 252 of first housing 281 is alongside first sidewall 251 of second housing 282, the differing lengths of branches 271 and 272 in bifurcation member 27" of adapter 400 can help to prevent such a coming together of housings 281, 282. Thus, adapter 400 provides an option encouraging a minimal thickness in adapting extensions 117 to device 20, the minimal thickness being approximately equal to or only slightly greater than that defined between first and second sidewalls 251, 252 of each of housings 281, 282. Of course, it should be appreciated that any of adapters 200, 300 and 300' may be implanted in such a slimmer configuration, if desired. The thicker configuration of adapters 200, 300 and 300' as shown in FIGS. 2D, 3B, and 3C, respectively, may be particularly preferred for those situations when an new pocket is created for device 20 and it is desirable for the adapter to fit snugly in the old pocket from which the old device has been explanted. The slimmer configuration of any of the adapters may be preferred if both device 20 and the adapter need to fit together within a newly created pocket.

FIG. 4B further illustrates the system including optional sleeves 40, for example, formed, by an extrusion or molding process, from medical grade silicone, extending around each of extension plugs 172 and the corresponding housing 281, 282 to bridge a junction therebetween. Sleeves 40 may provide for additional sealing and/or retention at an interface of the junction between each plug 172 and the corresponding housing 281, 282. An optional groove 45 shown extending about an outer surface of sleeves 40 may provide an interface for a securing element, for example a suture; sleeve 40 may include more than one of groove 45. Sleeves 40 may be pre-assembled onto housings 281, 282 or onto extension plugs 172, and may be initially slid back or rolled back thereon during insertion of plugs 172 into housings 281, 282. With reference back to FIG. 3B, a similar optional sleeve 30 is shown with dashed lines; optional sleeve 30 is sized to fit around both housings 281, 282 and the corresponding plugs 172 coupled thereto.

In the foregoing detailed description, the invention has been described with reference to specific embodiments. However, it may be appreciated that various modifications and changes can be made without departing from the scope of the invention as set forth in the appended claims.

We claim:

1. An adapter for coupling a pair of implantable neurostimulator lead extension plugs to a connector port of a neurostimulator device; each plug of the pair of plugs including first and second connector terminals extending side-by-side; each of the first and second connector terminals of each plug including a terminal pin contact and a contact surface spaced apart from the pin contact along a length of the corresponding connector terminal; the adapter comprising:

- an elongate body and eight elongate conductors extending therein;
- a connector coupled to a first end of the elongate body, the connector including eight contacts, each of the eight connector contacts for electrical coupling with a corresponding device contact mounted within the connector port of the device, and each of the eight connector contacts coupled to a corresponding conductor of the eight elongate conductors;
- a flexible bifurcation member coupled to a second end of the elongate body, the member including first and second branches; and
- a first housing coupled to the first branch and a second housing coupled to the second branch;
- each of the first and second housings including a first sidewall, a second sidewall, opposite the first sidewall, a first face extending between the first and second sidewalls, a second face, opposite the first face and extending between the first and second sidewalls, a third face extending between the first and second sidewalls and between the first and second faces, a fourth face, opposite the third face and extending between the first and second sidewalls and between the first and second faces, a first port and a second port;
- each of the first and second ports of each of the first and second housings including a first housing contact and a second housing contact, each of the first and second housing contacts coupled to a corresponding connector contact via the corresponding lead wire extending from the elongate body and into the corresponding housing;
- the first port of each of the first and second housings extending, from an opening located on the first face of the corresponding housing, toward the second face of the corresponding housing;
- the second port of each of the first and second housings extending, from an opening located on the first face, toward the second face of the corresponding housing, between the first port and the fourth face of the corresponding housing;
- wherein the first and second port openings of each of the first and second housings provide for side-by-side insertion of the first and second connector terminals of one of the pair of extension plugs, in order that the first connector terminal of the plug be electrically coupled to the first and second housing contacts of the first port of the corresponding housing, and the second connector terminal of the plug be electrically coupled to the first and second housing contacts of the second port of the corresponding housing.

2. The adapter of claim 1, wherein the eight connector contacts are spaced apart from one another along a length of the connector.

3. The adapter of claim 1, wherein the elongate body and the bifurcation member, together, have a length between approximately 10 centimeters and approximately 20 centimeters.

4. The adapter of claim 1, wherein elongate body and the bifurcation member, together, have a length greater than approximately 40 cm.

5. The adapter of claim 1, wherein at least one of the first and second sidewalls of each of the first and second housings has a relatively flat outer surface extending alongside both of the corresponding housing ports.

6. The adapter of claim 1, wherein the first housing contact of each of the first and second housing ports of each of the first and second housings comprises a set screw mounted in a set screw block.

7. The adapter of claim 6, wherein each of the first and second housings further includes a first access port for the set screw of the corresponding first port, each first access port being located along the third face of the corresponding housing, and a second access port for the set screw of the corresponding second port, each second access port being located along the second face of the corresponding housing.

8. The adapter of claim 7, wherein the second face of each of the first and second housings extends at an angle greater than 0 degrees and less than 90 degrees with respect to the first face of the corresponding housing.

9. The adapter of claim 6, wherein each of the first and second housings further includes an access port for each of the set screws of the corresponding housing, and none of the access ports are located along either sidewall of the corresponding housing.

10. The adapter of claim 6, wherein at least one of the set screws of each of the first and second housings is mounted such that a shaft of the at least one set screw extends at an angle greater than 0 degrees and less than 90 degrees with respect to the first face of the corresponding housing.

11. The adapter of claim 6, wherein:
- the set screw of the first port of each of the first and second housings is mounted such that a shaft of the first port set screw extends approximately parallel with the first face of the corresponding housing; and
- the set screw of the second port of each of the first and second housings is mounted such that a shaft the second port set screw extends at an angle greater than 0 degrees and less than 90 degrees with respect to the first face of the corresponding housing.

12. The adapter of claim 1, wherein each of the first and second housings further includes a hole extending therethrough from the first sidewall to the second sidewall of the corresponding housing.

13. The adapter of claim 12, wherein each hole is lined with a reinforcing material.

14. The adapter of claim 12, wherein each hole is located in proximity to an intersection of the second and third faces of the corresponding housing.

15. The adapter of claim 12, wherein a deformation of the flexible bifurcation member allows for alignment of the hole of the first housing with the hole of the second housing.

16. The adapter of claim 1, wherein, when the flexible bifurcation member is un-deformed, the fourth face of the first housing faces in a direction approximately opposite of a direction in which the fourth face of the second housing faces.

17. The adapter of claim 16, wherein a deformation of the flexible bifurcation member allows the fourth faces of the first and second housings to face in a same general direction, such that an outer surface of one of the first and second sidewalls of the first housing faces toward an outer surface of one of the first and second sidewalls of the second housing.

18. The adapter of claim 17, wherein the flexible bifurcation member further includes a bending joint located between the first branch and the second branch thereof, the bending joint facilitating the deformation of the flexible bifurcation member.

19. The adapter of claim 1, wherein the flexible bifurcation member further includes a bending joint located between the first branch and the second branch thereof, the bending joint facilitating a deformation of the flexible bifurcation member to move the first and second housings with respect to one another.

20. The adapter of claim 1, wherein, when the flexible bifurcation member is un-deformed, the fourth faces of the first and second housings face in a same general direction.

21. The adapter of claim 1, wherein, when the flexible bifurcation member is un-deformed, the first and second branches both extend along a plane, the first and second sidewalls of each of the first and second housings extend approximately parallel to the plane, and the first housing is offset from the second housing in a first direction along the plane.

22. The adapter of claim 21, wherein a deformation of the flexible bifurcation member allows alignment of the first housing with the second housing such that an outer surface of one of the first and second sidewalls of the first housing is located alongside and faces toward an outer surface of one of the first and second sidewalls of the second housing.

23. The adapter of claim 1, wherein, when the flexible bifurcation member is un-deformed, the first and second branches both extend along a plane, the first and second sidewalls of each of the first and second housings extend approximately parallel to the plane, and the first housing is offset from the second housing in a first direction along the plane and in a second direction along the plane, the second direction approximately perpendicular to the first direction.

24. The adapter of claim 1, wherein, when the flexible bifurcation member is un-deformed, the first and second branches both extend along a first plane and the first and second sidewalls of each of the first and second housings extend approximately parallel to a second plane, the second plane extending at an angle with respect to the first plane, the angle being greater than 0 degrees and less than or equal to 90 degrees.

25. The adapter of claim 1, wherein the first and second branches of the flexible bifurcation member are flexible to allow a deformation of the flexible bifurcation member to move the first and second housings with respect to one another.

26. The adapter of claim 1, wherein the flexible bifurcation member further includes a groove formed in at least one of the first and second branches in proximity to the corresponding housing.

27. An extension system for coupling an implantable neurostimulator lead to a connector port of a neurostimulator device, the system comprising:
   a lead extension including an elongate body, a connector port, coupled to a first end of the elongate body, for receiving a connector terminal of the neurostimulator lead, and an extension plug coupled to a second end of the elongate body, the extension plug including first and second connector terminals extending side-by-side; each of the first and second plug connector terminals including a terminal pin contact and a contact surface spaced apart from the pin contact along a length of the corresponding plug connector terminal; and
   an adapter comprising:
      an elongate body and eight elongate conductors extending therein;
      a connector coupled to a first end of the elongate body, the connector including eight contacts, each of the eight connector contacts for electrical coupling with a corresponding device contact mounted within the connector port of the device, and each of the eight connector contacts coupled to a corresponding conductor of the eight elongate conductors;
      a flexible bifurcation member coupled to a second end of the elongate body, the member including first and second branches; and
      a first housing coupled to the first branch and a second housing coupled to the second branch;
      each of the first and second housings including a first sidewall, a second sidewall, opposite the first sidewall, a first face extending between the first and second sidewalls, a second face, opposite the first face and extending between the first and second sidewalls, a third face extending between the first and second sidewalls and between the first and second faces, a fourth face, opposite the third face and extending between the first and second sidewalls and between the first and second faces, a first housing port and a second housing port;
      each of the first and second housing ports of each of the first and second housings including a first housing contact and a second housing contact, each of the first and second housing contacts coupled to a corresponding connector contact via the corresponding lead wire extending from the elongate body and into the corresponding housing;
      the first port of each of the first and second housings extending, from an opening located on the first face of the corresponding housing, toward the second face of the corresponding housing;
      the second port of each of the first and second housings extending, from an opening located on the first face, toward the second face of the corresponding housing, between the first port and the fourth face of the corresponding housing;
      wherein the first and second port openings of each of the first and second housings provide for side-by-side insertion of the first and second connector terminals of the extension plug, in order that the first connector terminal of the plug be electrically coupled to the first and second housing contacts of the first port of the corresponding housing, and the second connector terminal of the plug be electrically coupled to the first and second housing contacts of the second port of the corresponding housing.

28. The system of claim 27, wherein the eight connector contacts of the adapter are spaced apart from one another along a length of the adapter connector.

29. The system of claim 27, wherein the elongate body and the bifurcation member of the adapter, together, have a length between approximately 10 centimeters and approximately 20 centimeters.

30. The system of claim 27, wherein the elongate body and the bifurcation member of the adapter, together, have a length greater than approximately 40 centimeters.

31. The system of claim 27, wherein at least one of the first and second sidewalls of each of the first and second adapter housings has a relatively flat outer surface extending alongside both of the corresponding housing ports.

32. The system of claim 27, wherein the first housing contact of each of the first and second housing ports of each of the first and second adapter housings comprises a set screw mounted in a set screw block.

33. The system of claim 32, wherein each of the first and second adapter housings further includes a first access port for the set screw of the corresponding first port, each first access port being located along the third face of the corresponding housing, and a second access port for the set screw of the corresponding second port, each second access port being located along the second face of the corresponding housing.

34. The system of claim 33, wherein the second face of each of the first and second housings extends at an angle greater than 0 degrees and less than 90 degrees with respect to the first face of the corresponding housing.

35. The system of claim 32, wherein each of the first and second adapter housings further includes an access port for each of the set screws of the corresponding housing, and none of the access ports are located along either sidewall of the corresponding housing.

36. The system of claim 32, wherein at least one of the set screws of each of the first and second adapter housings is mounted such that a shaft of the at least one set screw extends at an angle greater than 0 degrees and less than 90 degrees with respect to the first face of the corresponding housing.

37. The system of claim 32, wherein:
the set screw of the first port of each of the first and second adapter housings is mounted such that a shaft of the first port set screw extends approximately parallel with the first face of the corresponding housing; and
the set screw of the second port of each of the first and second adapter housings is mounted such that a shaft the second port set screw extends at an angle greater than 0 degrees and less than 90 degrees with respect to the first face of the corresponding housing.

38. The system of claim 27, wherein each of the first and second adapter housings further includes a hole extending therethrough from the first sidewall to the second sidewall of the corresponding housing.

39. The system of claim 38, wherein each hole is lined with a reinforcing material.

40. The system of claim 38, wherein each hole is located in proximity to an intersection of the second and third faces of the corresponding adapter housing.

41. The system of claim 38, wherein a deformation of the flexible bifurcation member of the adapter allows for alignment of the hole of the first adapter housing with the hole of the second adapter housing.

42. The system of claim 27, wherein, when the flexible bifurcation member of the adapter is un-deformed, the fourth face of the first adapter housing faces in a direction approximately opposite of a direction in which the fourth face of the second adapter housing faces.

43. The system of claim 42, wherein a deformation of the flexible bifurcation member allows the fourth faces of the first and second adapter housings to face in a same general direction, such that an outer surface of one of the first and second sidewalls of the first adapter housing faces toward an outer surface of one of the first and second sidewalls of the second adapter housing.

44. The system of claim 43, wherein the flexible bifurcation member further includes a bending joint located between the first branch and the second branch thereof, the bending joint facilitating the deformation of the flexible bifurcation member.

45. The system of claim 27, wherein the flexible bifurcation member of the adapter further includes a bending joint located between the first branch and the second branch thereof, the bending joint facilitating a deformation of the flexible bifurcation member to move the first and second adapter housings with respect to one another.

46. The system of claim 27, wherein, when the flexible bifurcation member of the adapter is un-deformed, the fourth faces of the first and second adapter housings face in a same general direction.

47. The system of claim 27, wherein, when the flexible bifurcation member of the adapter is un-deformed, the first and second branches thereof both extend along a plane, the first and second sidewalls of each of the first and second adapter housings extend approximately parallel to the plane, and the first adapter housing is offset from the second adapter housing in a first direction along the plane.

48. The system of claim 47, wherein a deformation of the flexible bifurcation member allows alignment of the first adapter housing with the second adapter housing such that an outer surface of one of the first and second sidewalls of the first adapter housing is located alongside and faces toward an outer surface of one of the first and second sidewalls of the second adapter housing.

49. The system of claim 27, wherein, when the flexible bifurcation member of the adapter is un-deformed, the first and second branches thereof both extend along a plane, the first and second sidewalls of each of the first and second adapter housings extend approximately parallel to the plane, and the first adapter housing is offset from the second adapter housing in a first direction along the plane and in a second direction along the plane, the second direction approximately perpendicular to the first direction.

50. The system of claim 27, wherein, when the flexible bifurcation member of the adapter is un-deformed, the first and second branches thereof both extend along a first plane and the first and second sidewalls of each of the first and second adapter housings extend approximately parallel to a second plane, the second plane extending at an angle with respect to the first plane, the angle being greater than 0 degrees and less than or equal to 90 degrees.

51. The system of claim 27, wherein the first and second branches of the flexible bifurcation member of the adapter are flexible to allow a deformation of the flexible bifurcation member to move the first and second adapter housings with respect to one another.

52. The system of claim 27, wherein the flexible bifurcation member of the adapter further includes a groove formed in at least one of the first and second branches in proximity to the corresponding housing.

53. The system of claim 27, further comprising a sleeve sized to fit about an outer surface of the extension plug and about one of the first and second adapter housings when the first and second connector terminals of the extension plug are inserted within the first and second ports, respectively, of the one of the first and second adapter housings.

54. The system of claim 53, wherein the sleeve includes a groove formed in an outer surface thereof.

55. The system of claim 27, further comprising:
another lead extension including an elongate body and an extension plug coupled to an end thereof, the plug of the other extension including first and second connector terminals extending side-by-side; and
a sleeve sized to fit about both extension plugs and both of the first and second housings, when the first and second connector terminals of each of the extension plugs are inserted within the first and second ports, respectively, of the corresponding adapter housing.

* * * * *